United States Patent
Baiu

(10) Patent No.: US 9,669,116 B2
(45) Date of Patent: Jun. 6, 2017

(54) WATER-EQUIVALENT PHANTOM

(71) Applicant: Gammex, Inc., Middleton, WI (US)

(72) Inventor: Cristel Baiu, Madison, WI (US)

(73) Assignee: Gammex, Inc., Middleton, WI (US)

( * ) Notice: Subject to any disclaimer, the term of this patent is extended or adjusted under 35 U.S.C. 154(b) by 235 days.

(21) Appl. No.: 14/449,928

(22) Filed: Aug. 1, 2014

(65) Prior Publication Data

US 2016/0015836 A1 Jan. 21, 2016

Related U.S. Application Data

(60) Provisional application No. 62/026,391, filed on Jul. 18, 2014.

(51) Int. Cl.
*A61K 49/04* (2006.01)

(52) U.S. Cl.
CPC ...... *A61K 49/0419* (2013.01); *A61K 49/0409* (2013.01); *A61K 49/04* (2013.01)

(58) Field of Classification Search
None
See application file for complete search history.

(56) References Cited

U.S. PATENT DOCUMENTS

| | | |
|---|---|---|
| 5,335,260 A | 8/1994 | Arnold |
| 5,625,137 A | 4/1997 | Madsen et al. |
| 5,902,748 A | 5/1999 | Madsen et al. |
| 6,190,915 B1 | 2/2001 | Madsen et al. |
| 6,238,343 B1 | 5/2001 | Madsen et al. |
| 6,352,860 B1 | 3/2002 | Madsen et al. |
| 6,974,254 B2 | 12/2005 | Paliwal et al. |
| 7,252,434 B2 | 8/2007 | Jaradat |
| 8,480,407 B2 | 7/2013 | Campbell et al. |
| 8,517,608 B1 | 8/2013 | Arnold |
| 8,588,365 B2 | 11/2013 | Lang et al. |

OTHER PUBLICATIONS

Homolka et al. (Phys. Med. Biol. 2002, 47, 2917-2923).*
Nigg et al. (Med. Phys. 2000, 27, 359-367).*
Hack, Joshua, "Development and implementation of quality-assurance standards for external beam intensity modulated radiation therapy" (2009), Theses and Dissertations, Paper 1066.*
Burton et al. (Huntsman Epoxy Formulations Using Jeffamine® Polyetheramines Apr. 27, 2005 does not disclose JEFFAMINE®).*
Tello et al. (Med. Phys. 1995, 22, 1177-1189).*
Chong et al, "Separation of bone from iodine- and gadolinium-based contrast agents using dual energy CT", Physics of Medical Imaging, vol. 6913, 2008.
Civ, "Tissue Substitues in Radiation Dosimetry and Measurement (Report 44)", Commission Meeting 2014. http://icru.org/home/reports/tissue-substitutes-in-radiation-dosimetry-and-measurement-report-44.
Hubbell et al., "Tables of X-Ray Mass Attenuation Coefficients and Mass Energy-Absorption Coefficients from 1 keV to 20 MeV for Elements Z=1 to 92 and 48 Additional Substances of Dosimetric Interest", Radiation Physics Division, Table 4, Brain, Grey/White Matter, U.S. Secretary of Commerce on behalf of the United States of America, 1996.
Liu et al., "Evaluation of two water-equivalent phantom materials for output calibration of photon and electron beams", Med. Dosim, vol. 28, No. 4, Abstract, 2003.
Ramaseshan et al., "Dosimetric evaluation of Plastic Water Diagnostic Therapy", Journal of Applied Clinical Medical Physics, vol. 9; No. 2, 2008.
Thomadsen et al., "Evaluation of water-equivalent plastics as phantom material for electron-beam dosimetry", Med. Phys., vol. 22, No. 3, 1995.
White et al, "Epoxy resin based tissue substitutes", British Journal of Radiology, vol. 50, pp. 814-821, 1977.
Yohannes et al., "A formulation of tissue- and water-equivalent materials using the stoichiometric analysis method for CT-number calibration in radiotherapy treatment planning", Physics in Medicine and Biology, 57: pp. 1173-1190, 2012.
Gammex Solid Water and TEM Guide by Gammex, Inc., Feb. 2012.
Certified Therapy Grade Solid Water by Gammex, Inc., Jun. 2008.
Convenient Packages of Solid Water by Gammex, Inc., Sep. 2010.
Certified Therapy Grade Solid Water, Gammex 457-CTG, by Gammex, Inc., http://www.gammex.com/n-portfolio/productpage.asp?id=287&category=Radiation Oncology&name=Certified Therapy, website visited 2014.
Tissue Equivalent Materials by Gammex, Inc., Jun. 2008.
Tissue Characterization Phantom, Model 467 User's Guide by Gammex, Inc., 2004.

* cited by examiner

*Primary Examiner* — Michael G Hartley
*Assistant Examiner* — Melissa Perreira
(74) *Attorney, Agent, or Firm* — Andrus Intellectual Property Law, LLP

(57) ABSTRACT

A composition for use in radiology includes glass micro bubbles, Araldite, Jeffamine, magnesium oxide, and polyethylene. Another composition or use in radiology may include glass micro bubbles, an epoxy, acrylic, or polyurethane, and polyethylene. This composition may result in an elemental composition including carbon, oxygen, hydrogen, nitrogen, calcium, and magnesium. A composition for use in radiology may include glass micro bubbles, araldite, jeffamine, calcium carbonate, magnesium oxide, polyethylene, and a pigment and the composition includes an elemental composition including carbon, oxygen, hydrogen, nitrogen, calcium, silicon, and magnesium.

20 Claims, 2 Drawing Sheets

WATER-EQUIVALENT PHANTOM

CROSS-REFERENCE THE RELATED APPLICATION

The present application claims priority of U.S. Provisional Patent Application No. 62/026,391, filed on Jul. 18, 2014, the content of which is hereby incorporated herein by reference in its entirety.

BACKGROUND OF THE INVENTION

The present disclosure is related to the field of radiographic imaging, radiotherapy and analysis thereof. More specifically, the present disclosure is related to water-equivalent phantoms for calibration and/or quality assurance purposes in radiology.

X-rays and other radiological techniques are important diagnostic and/or therapeutic tools. However, the measurement of absorbed doses within and around radiated body tissue necessitates calibration of these radiological devices with phantoms constructed of carefully selected materials. The use of such phantoms permit the determination of absorbed doses and correction factors for use radiography or radiotherapy when information on the energy and nature of charged particles at the point of interest is incomplete or fragmentary.

In such calibration or quality assurance methods or processes, water equivalent phantoms provide an important role. Radiodensity refers to the relative ability of a material to absorb or block passage of electromagnetic radiation, particularly X-rays. Radiodensity is often described according to the Hounsfield scale measured in the Hounsfield unit (HU), which is a common unit for CT number. The Hounsfield unit scale is a linear transformation of linear attenuation coefficient measurements where the radiodensity of distilled miter at standard pressure and temperature (STP) is defined as zero HI the radiodensity of air at standard temperature and pressure (STP) is defined as −1,000 HU. The radiodensity of a material such as bone or calcification may be on the order of 1,000 HU. In order to calibrate a radiographic system to the Hounsfield unit scale, a comparison must be made to distilled water. Imaging a water itself presents the natural problem of containing the water for imaging and the tendency of water to transmit motion, noise, or other vibration, resulting in movement of the water to be imaged. Therefore, a solid material that exhibits the radiographic properties of water is desired for calibration and quality control. Solid material water-equivalent phantoms have been available for approximately 30 years. One challenge in the construction of water-equivalent solid materials is the inherent requirement that the water-equivalent materials have a chemical composition largely different than that of distilled water, yet must be embodied in a material that is solid at standard temperature and pressure. Such material is typically an epoxy, acrylic, or polyethylene base, which is modified by other elements to achieve a desired elemental composition, physical density, effective atomic number, electron density, and radiodensity, such that the attenuating and scattering characteristics closely resemble that of water.

The International Commission on Radiation Units and Measurements (ICRU) in its Report 44 entitled "Tissue Substitutes in Radiation Dosimetry and Measurement" provides approximate elemental, radiographic, and other physical properties for average body tissues, including water. This report, states that a water-equivalent solid phantom must not introduce more than 1% uncertainty to the absorbed dose. If total uncertainty is more than 1%, appropriate correction factors are required to be applied. Therefore, a water-equivalent solid phantom with radiographic properties within 1% that of distilled water is desirable in the field to avoid such requirement for correction factors.

A typical radiation therapy process begins by scanning patient using computed tomography (CT). The resulting three-dimensional CT image data is used in the treatment plan to calculate patient inhomogeneities. To perform true quality assurance (QA) it is ideal to simulate the entire treatment process. Simulation of the entire treatment processes requires scanning a phantom using the CT and then using the same phantom for radiotherapy measurements. For example to perform patient-specific intensity modulated radiation therapy (IMRT) verification measurements, the patient fluence is transferred to the water-equivalent solid phantom and a forward dose calculation is performed. The calculated dose is then compared to the point dose and to the dose distribution measured in the phantom. In this process, it is desirable that the phantom characteristics match attenuation and absorption properties in the diagnostic range (5 keV-150 keV) and therapeutic radiation energies (greater than 1 MeV).

The inventor has recognized that a need exists for new water-equivalent solid phantoms that exhibit a high degree of accuracy to natural water over the entire range of diagnostic and therapeutic energies.

SUMMARY OF THE INVENTION

Compositions for use in radiology including radiodiagnostics, radiography, radiotherapy, calibration of devices and treatment planning applications as well as other applications are provided herein. In particular the compositions are water phantoms.

In one aspect, the compositions include 2.9-3.3% Glass Micro Bubbles (w/w), 54-67% Araldite (w/w), 20-33% Jeffamine (w/w), 3-5% $CaCO_3$ (w/w), 1-3% MgO (w/w), and 8-12% Polyethylene (w/w). These compositions may include pigments and may have an elemental composition including 64-67% carbon (w/w), 18-21% oxygen (w/w), 7-10% hydrogen (w/w), 1-3.5% nitrogen (w/w), 0.5-3% calcium (w/w), 0.5-2.5% magnesium (w/w). The composition may also contain less than 1% chlorine, boron, aluminum, sodium, and sulfur.

In another aspect, the compositions include 2.9-3.3% glass micro bubbles (w/w), 60-90% epoxy, acrylic or polyurethane (w/w), and 8-12% Polyethylene (w/w), with a resulting elemental composition of 64-67% carbon (w/w), 18-21% oxygen (w/w), 7-10% hydrogen (w/w), 1-3.5% nitrogen (w/w), 0.5-3% calcium (w/w), 0.5-2.5% magnesium (w/w). These compositions may thriller include pigments and the epoxy may be a two part epoxy resin systems with a ratio of part A (resin) to part B (hardener) is between 10 to 3 and 1 to 1. In additional embodiments, the epoxy system may be a three party epoxy system. The composition may also contain less that 1% chlorine, boron, aluminum, sodium, and sulfur.

In still another aspect the composition includes 3.09% (w/w) glass microbubbles, 57.88% (w/w) Araldite, 23.15% (w/w) Jeffamine, 3.89% (w/w) Calcium Carbonate ($CaCO_3$); 1.80% (w/w) Magnesium Oxide (MgO), 9.98% (w/w) Polyethylene (PE)$((C_2H_4)NH_2)$, 0.2% (w/w) $Na_6Al_6Si_6O_{24}S_4$ or $Si_4O_{10}(OH)_2Mg_3$—$Co_3Ca$—Al with an elemental composition of 65.81% carbon (w/w), 19.36% oxygen (w/w), 8.14% hydrogen (w/w), 2.21% nitrogen (w/w) 1.78% calcium (w/w), 1.14% silicon (w/w), and 1.11% magnesium (w/w). The composition may also contain less than 1% chlorine, boron, aluminum, sodium, and sulfur.

BRIEF DESCRIPTION OF THE DRAWINGS

Figure depicts an exemplary embodiment of a CT image of an exemplary embodiment of a water-equivalent phantom.

DETAILED DISCLOSURE

Figure 1:
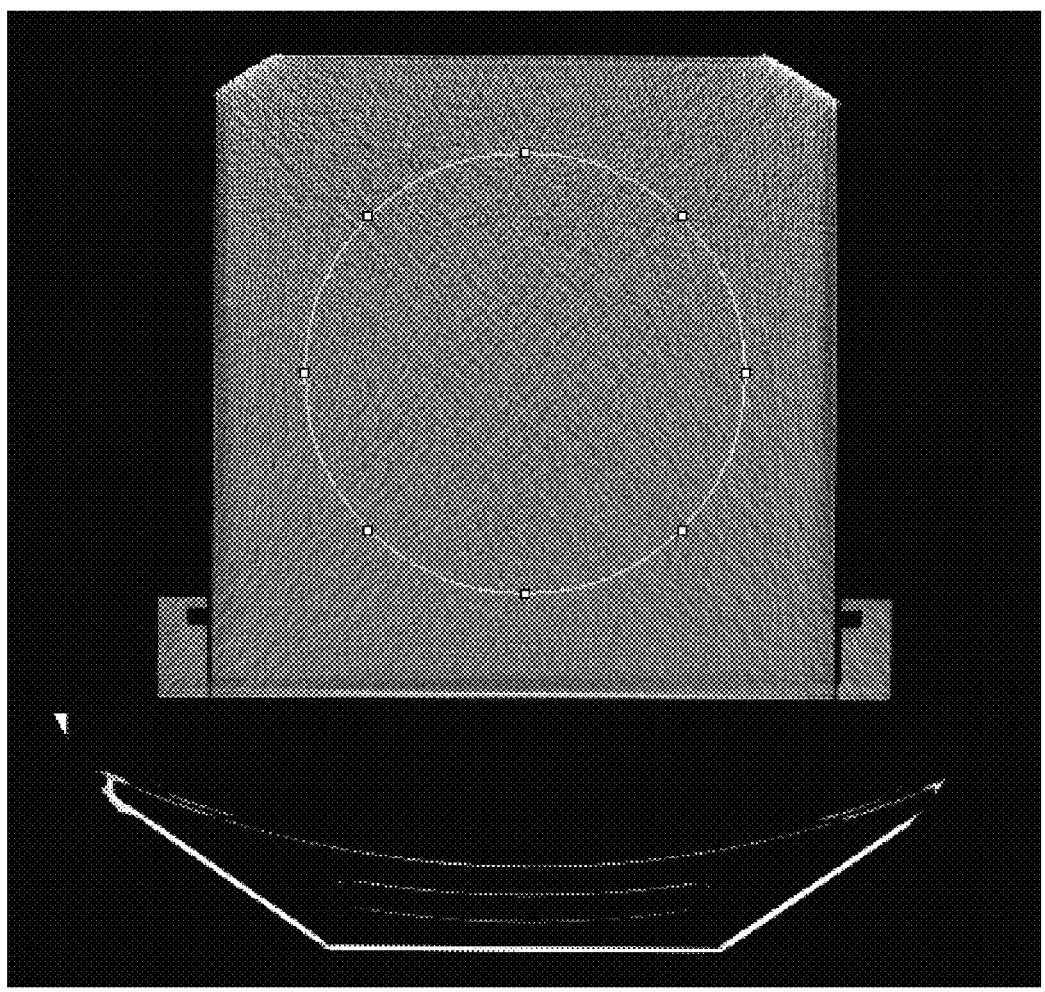

A water-equivalent solid phantom for use in calibration and quality assurance (QA) applications for radiology, including radiography and radiotherapy, is disclosed herein. In non-limiting examples, radiography ms include computed tomography (CT) imaging applications and radiotherapy may include, but is not limited to, intensity-modulated radiation therapy (IMRT). However, it is recognized that embodiments of phantoms as disclosed herein may also be used with other imaging modalities as ma be recognized by a person of ordinary skill in the art, including, but not limited to x-ray. It is further recognized that embodiments of phantoms as disclosed herein may also be used in QA applications for other types of radiotherapy, including, but not limited to proton or other particle therapies. The Hounsfield scale is the standard scale by which radiodensity of objects and their materials are characterized when imaged via CT.

The Hounsfield scale uses the radiodensity of water at standard temperature and pressure (STP) as the reference zero value. Therefore, a phantom that accurately and consistently mimics the chimerical, density, and radiological properties of water, or physiological structures containing water, is desired for calibration and quality assurance of these radiological systems.

In radiography, a correction factor may be repeatedly recalculated far a specific radiographic imaging device to normalize a X-ray radiation received at the imaging collector to the Hounsfield unit scale.

In still further embodiments, the water-equivalent material may alternatively be desired to mimic a material containing water, but with a different radiodensity, for example interstitial fluid or other generalized body tissue (which is often predominantly water). In such embodiments, it is desirable to achieve an alternative Hounsfield score, while maintaining the consistency and accuracy in the material as described above. In non-limiting exemplary embodiments as disclosed in further detail herein, for example, a water-equivalent phantom material used to mimic generalized body tissue and interstitial fluid may have a Hounsfield score between 5-20 HU, or more specifically 15-7 HU, or more specifically 16 HU. Exemplary embodiments such as these may be achieved as disclosed herein within the scope of the present disclosure. Other Hounsfield scales may be achieved along the Hounsfield scale while remaining within the embodiment of compositions as disclosed herein.

The compositions include 2.9-3.3% Glass Micro Bubbles (w/w), 54-67% Araldite (w/w), 20-33% Jeffamine (w/w) 3-5% $CaCO_3$ (w/w), 1-3% MgO (w/w, and 8-12% Polyethylene (w/w). These compositions may include pigments and may have an elemental composition including 64-67% carbon (w/w), 18-21% oxygen (w/w), 7-10% hydrogen (w/w), 1-3.5% nitrogen (w/w), 0.5-3% calcium (w/w), 0.5-2.5% magnesium (w/w). The composition may also contain less than 1% chlorine, boron, aluminum, sodium, and sulfur. Further compositions include 2.9-3.3% Glass Micro Bubbles (w/w), 60-90% of an epoxy, acrylic or polyurethane (w/w), and 8-12% Polyethylene (w/w), with a resulting elemental composition of 64-67% carbon (w/w), 18-21% oxygen (w/w), 7-10% hydrogen (w/w), 1-3.5% nitrogen (w/w), 0.5-3% calcium (w/w), 0.5-2.5% magnesium (w/w). These compositions may further include pigments and the epoxy may be a two part epoxy resin systems with a ratio of part A (resin) to part B (hardener) is between 10 to 3 and 1 to 1. The composition may also contain less than 1% chlorine, boron, aluminum, sodium, and sulfur. The epoxy may be Araldite and Jeffamine or may be another epoxy resin system such as CB1, CB2, CB3 or CB4. These resins may include a resin selected from Araldite, Trimethylhexamethylenediamine, Epoxide No. 7, Epikote and combinations thereof and the hardener may be selected from Jeffamine, Synolide, aminohexanes, polyoxypropylenetriamines or combinations thereof.

An exemplary embodiment of the water-equivalent solid phantom material as disclosed herein includes the following ingredients: 3.09% (w/w) glass microbubbles, 57.88% (w/w) Araldite, 23.15% (w/w) Jeffamine, 189% (w/w) Calcium Carbonate ($CaCO_3$); 1.80% (w/w) Magnesium Oxide (MgO), 9.98% (w/w) Polyethylene ($VEX(C_2H_4)_nNH_2$). Still further embodiments include 0.2% (w/w) pigment, which is exemplarily $Na_6Al_6Si_6O_{24}S_4$. The elemental composition of the phantom is 65.81% carbon (w/w), 19.36% oxygen (w/w), 8.14% hydrogen (w/w), 2.21% nitrogen (w/w) 1.78% calcium (w/w), 1.14% silicon (w/w), 1.11% magnesium (w/w), 0.14% chlorine (w/w), 0.05% boron (w/w), 0.03% aluminum (w/w), 0.2% sodium (w/w), and 0.03% sulfur (w/w). A water equivalent solid phantom material composes 2.9-3.3% (w/w) glass micro bubbles, 54-67% (w/w) Araldite, 20-33% (w/w) Jeffamine, 3-5% (w/w) $CaCO_3$, 1-3% (w/w) MgO, 8-12% (w/w) Polyethylene, and 0-1% (w/w) pigment in one embodiment.

The electron density and effective atomic number of the solid water phantom is suitably less than 1.0% of the natural material and preferably less than 0.5% of the natural material. Variations in the pigment used and the quality of the pigment may require recalculation of the other ingredients to obtain the same radiographic results. For example if the pigment is a calcium chloride based pigment, the quantity of the calcium chloride added to the phantom will be reduced to compensate for the calcium chloride in the pigment. In exemplary embodiments, the resulting water equivalent material has a physical density of 1.03+/−0.03 g/cc. In still further embodiments, the physical density is 1.030+/−0.030 g/cc.

The ingredients listed above assume a nominal density of the glass microbubbles of 0.22 g/CC and results in an electron density and effective atomic number of the material within better than 0.5% from distilled water. Variation of the physical density of glass microbubbles (typical +/−15%) requires adequate changes in the percentages of the other ingredients to maintain the physical density, electron density, effective atomic number and calculated CT number within the target. The Araldite/Jeffamine Epoxy system can be changed within a range of 100/30 proportion of to 100/100 to achieve other desired mechanical properties of the material. Specific examples include 100/40 and 100/43 ratios. The Araldite/Jeffamine epoxy system should be between 60 and 90% of the final composition. This will require the re-adjustment of the concentrations of the other ingredients.

In an embodiment, the glass microspheres are S22 Glass Bubbles available from 3M. The Glass Bubbles have an 80% size distribution between 20 microns and 65 microns and in general resemble the chemical properties of soda-lime-borosilicate glass.

ARALDITE is as structural adhesive available from Huntsman Advanced Materials. Araldite is an epoxy adhesive with high temperature and chemical resistances, low shrinking, and high resistance to water and as variety of other chemicals. Araldite GY 6010 has chemical formula $CH_{21}H_{24}O_4(C_{18}H_{20}O_3)n$ and a molecular weight of 364-384, Araldyte GY 6010 has the color and consistency of honey and will also crystallize at temperatures below 18 Celsius. Warming up this material at temperatures above 60 Celcius eliminates the crystals and lowers the viscosity making it easier to degas.

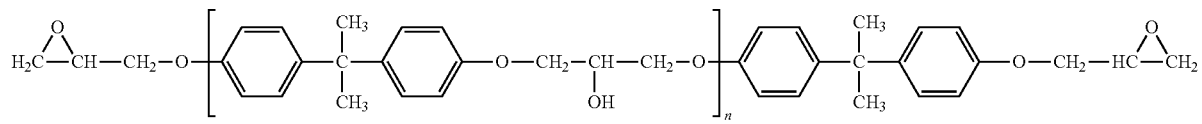

JEFFAMINE is as polyetheramine which contains primary amino group attached to the end or a polyether backbone. The polyether backbone is normally based on propylene oxide, ethylene mode or a mixture of propylene oxide and ethylene oxide. In an exemplary embodiment, the Jeffamine is a propylene oxide triamine prepared by the reaction of propylene oxide with triol initiator, followed by animation or the trammel hydroxyl groups and may be exemplified by the following structure

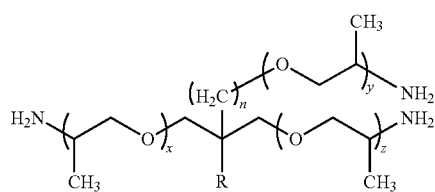

Exemplarily, this compound has molecular weight of 440.

The polyethylene used in the compositions described herein was Microthene FN510-00 a microfine polyolefin powder with as density of 0.023 obtained from Equistar Chemicals, Houston, Tex. Other low density polyethylene powders may be substituted for the polyethylene used herein. The magnesium oxide used herein was a high purity technical grade obtained from Premier Chemicals, Middleburg Heights, Ohio. The calcium carbonate used herein was a 5 micron grain size obtained from Chidley & Petro Co., Arlington Heights, Ill. Those of skill in the art will appreciate that these materials may be substituted with others of similar grade from other suppliers.

The ingredients are all weighed and placed on a mixing bowl. The mixing process takes place in a vacuumed chamber to eliminate air bubbles for about 40 minutes. The mix is then transferred in molds to create slabs or other desired slabs. Alternatively the powders can be pre-mixed with one part of the epoxy system (e.g. Araldite) and stored until mixed with the second part of the epoxy system. Cooling down the Jeffamine at temperature around 10 Celsius before is added to the mix assures a higher viscosity and therefore a more uniform distribution of the solid ingredients (heavier ingredients will not sink and low density ingredients will not float).

In still further exemplary embodiment, the inventor has recognized that the above formulation results in a water-equivalent phantom that highly mimics the radiological properties of water, however, the inventor has also recognized that the resulting water-equivalent phantom material has a translucent grey/taupe appearance. Without the pigment the electron density varies by about 0.1% and the effective atomic number by about 0.5% but are still within 1% of distilled water. Based upon consumer preferences, it is desirable to produce a water-equivalent phantom material with an improved esthetic appearance. However, due to the precise tolerances required for the chemical and radiographic properties of the water-equivalent phantom, the inventor recognizes any additive will adversely impact the accuracy of the water mimicking properties of the disclosed phantom. In fact, many available color solutions are unsuitable for this purpose as introduction of such pigments causes significant impact on the radiographic properties of the resulting material. Even with selecting for a pigment composition that minimizes impact on the radiographic properties of the material, the composition must be adjusted to accommodate such pigment in order to maintain the high degree of radiographic equivalency achieved in the material as highlighted above. Therefore, in an exemplary embodiment, the water-equivalent solid material includes 0.2% $Na_6Al_6Si_6O_{24}S_4$ blue pigment. The introduction of this pigment is accompanied by modifying the composition to account for the radiodensity, elemental composition, physical density, electron density, effective atomic number, and/or alternating and scattering characteristics of the pigment in the process described above.

The above described pigment results in a blue colored phantom, while for example $Si_4O_{10}(OH)_2Mg_3$—$Co_3Ca$—$Al$ will result in a lavender color. While these exemplary pigments are sulfur based, it is further recognized that in some embodiments a phosphorus based pigment may also be used with similar modifications as described above. In still further embodiments, a $CaCO_3$ pigment or other organic pigments may be used.

In an exemplary embodiment, the a water-equivalent material as disclosed herein, may be used in a calibration device for radiographic applications or formed into a quality assurance device for radiotherapeutic applications. In still further exemplary embodiments, the water-equivalent material as disclosed herein may be used in calibration device for ultrasound applications or in a device for use in radiotherapy planning.

In an exemplary embodiment of a device used for radiographic calibration, the calibration device includes a device body. The device body is exemplarily constructed of the water-equivalent solid material as described above. The device body further includes a plurality of slots or recesses which are shaped and dimensioned such as to receive inserts as will be described in further detail herein. In an exemplary embodiment, the body further includes alignment structures either in the surface of the calibration device or imbedded within the calibration device. The alignment structures are comprised of a material at one end or the other of the Hounsfield scale (e.g. air, metal, or another radio-transparent or radio-opaque material). These materials selected for the alignment structures present maximized contrast from the radio-neutral (0 HU) water-equivalent phantom material. The alignment structures are therefore easily identifiable in a resulting radiographic image and can thus be used to ensure or correct for positioning of the calibration device with respect to the radiographic device.

A plurality of tissue equivalent inserts extend into the respective slots in the body. In embodiments, the tissue equivalent inserts may be solid phantoms constructed of materials as known in the art to mimic the radiographic properties of one or more materials or tissues as may be imaged or exposed during a radiographic or radio therapeutic procedure. In exemplary embodiments, the tissue equivalent materials, acknowledging the large percentage of water present in some tissues may be modified water-equivalent materials within the scope of the above description to achieve alternative Houndsfield scores. In further exemplary embodiments, such tissue equivalent inserts may be the Gammex 400 series of tissue equivalent materials, available from Gammex, Inc.

FIG. 1 depicts an exemplary embodiment of a CT image of an exemplary embodiment of the water-equivalent phantom. The exemplary embodiment of the water-equivalent phantom is the Certified Therapy Grade (CTG) SOLID WATER® HE material, available from Gammex, Inc. The CT Image of FIG. 1 exemplarily depicts an image-set of SOLID WATER® HE material for a square CTG slab, exemplarily serial number T19919-3 (size 30 cm×30 cm×5 cur), stood on edge. The image was exemplarity obtained using a DISCOVERY LS CT Scanner, available from General Electric Company. An examination of FIG. 1 highlights the consistency of the CT number achieved across the entire phantom.

Figure 2:
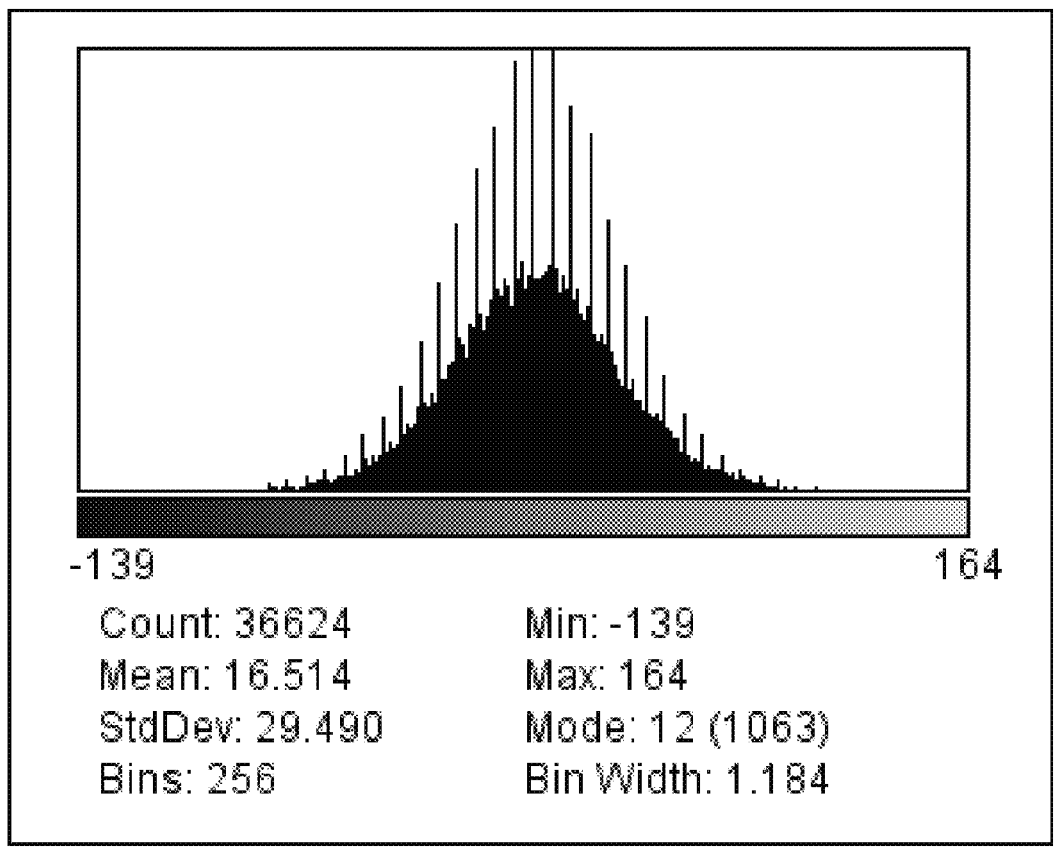
FIG. 2 is a histogram graph of CT number values obtained from a region of interest in the CT image of FIG. 1.

FIG. 2 is a histogram graph of CT number values obtained from a region of interest in the CT image of FIG. 1. The histogram is exemplarily based upon the Certified Therapy Grade (CTG) SOLID WATER® HE material based on 100 batches in the noncontiguous range of batch/serial numbers T19415-T20095. The histogram graph of FIG. 2 presents CT Number values within the circular region-of-interest (ROI) identified in the CT image of FIG. 1. The data was collected with a technique of 120 kVp and 240 mA. Note the top corners are cut-off due to the limited field-of-view of the CT Scanner. The histogram plot indicates the average CT Number for this particular ROI to be 16.5 HU. Since CT is an inherently noisy imaging modality, the image yields a notable distribution of CT Numbers measured within the ROI as seen by the histogram plot.

Table 1, below, presents the measured transmission test data exemplarily obtained as described above in therapeutic energy ranges as compared to the imaging energy ranges presented above with respect to FIGS. 1 and 2.

TABLE I

Measured Transmission Test Data

| Modality | Average Depth Ionization Value Relative to Water | Standard Deviation |
|---|---|---|
| 6 MV Photons (10.0 cm depth) | 1.0005 | 0.0051 |
| 18 MeV Electrons (4.4 cm depth) | 0.9948 | 0.0019 |

| Average Measured Physical Density [g/cc] | Standard Deviation [g/cc] |
|---|---|
| 1.0332 | 0.0009 |

In an exemplary embodiment of a method of calibrating, a radiographic device for imaging water using a solid water equivalent, a device specific correction factor is calculated in order to establish a relationship for a specific radiographic device between electron density ($\rho_3$) of various samples and the corresponding CT number in Hounsfield units (HU). The phantom is positioned onto a gantry of a radiographic device. The phantom may include a plurality of tissue equivalent materials or inserts. In an embodiment, the phantom includes at least one water equivalent material constructed in the compositions and/or manner as disclosed herein, although it will be recognized that in alternative embodiments, the phantom may comprise a plurality of a variety of tissue materials or inserts.

The phantom is aligned with the radiographic device for radiographic imaging, exemplarily CT imaging. In embodiments, the phantom may include visible or radiographically visible aligned markers to facilitate the alignment of the phantom with the radiographic device. The attenuation of the water equivalent material is measured with the radiographic device. In an exemplary embodiment, this measurement of the attenuation is represented in Hounsfield units. In an exemplary embodiment, the attenuations are measured for each of the tissue equivalent materials in the phantom. In exemplary embodiments, the accuracy and consistency of the water-equivalent material forming the structure of the phantom device provides a consistent baseline against which various correction factors for particular tissue-equivalent materials may be calculated.

Optionally, the measurements are repeated for a plurality of X-ray energies. In an exemplary embodiment, the plurality of X-ray energies may include 40 keV-140 keV, while other ranges, including but not limited to, 0.10 keV-150 keV may also be used, while narrower ranges or measurement at 1, 2, or another predetermined number of specific X-ray energies are made. From these measurements a device specific correction factor may be calculated from the measured attenuation and the electron density, in an exemplary embodiment, the correction factor may be calculated. In an exemplary embodiment, the Bethe formula may exemplarily be used; collection factors equal TAR{TAR($d_2$,A)/TAR($d_1$, A)}$(\rho_e)^{-1}$ where a is the field area and $d_1$ and $d_2$ are the distances of the point of interest to the top and bottom of the heterogeneity. In embodiments, the correction factor may be calculated specifically for the device for correction of water, while in alternative embodiments, correction factors vans be calculated for each of a plurality of different image tissues. In a still further embodiment, a generalized correction factor may be calculated for imaging of all samples by the specific device.

Optionally, the measured attenuations may be plotted against the known electron densities for each of the water or tissue equivalent materials. These plots may further be constructed at each of the plurality of X-ray energies at which the attenuation measurements are obtained. The plotting of the measured attenuation against normal electron densities may facilitate the calibration of the device specific correction factor as described above.

The device specific correction factor as calculated above may be applied to acquired radiographic images by the radiographic device to properly calibrate the CT number to the image tissues for that radiographic device.

In an exemplary embodiment of a device used for radiotherapeutic quality assurance (QA), the water-equivalent material may be formed into a device body. In an exemplary embodiment, the device body may be constructed as described above, however, in alternative embodiments, the device body may be constructed in an anatomically simulative form, or in a geometric shape such as a brick, sheet, or slab. In an exemplary embodiment, described in further detail herein, the water-equivalent phantom may be constructed of an embodiment of the water-equivalent material in the shape of a sheet of material with a defined thickness.

In a radiotherapy QA application, it may be desirable to confirm that the treatment isocenter will receive the prescribed and calculated radiation dose. In such an example, the radiation dose arrives at the target (e.g. cancerous tumor) after passing through tissue of the patient's body (which can comprise a high percentage of water) and therefore be represented by a modified water-equivalent phantom as described above. In as non-limiting example, the water-equivalent material used may be an embodiment with a Houndsfield score, e.g between 5-25 HU.

The depth of the target isocenter within the body of the patient is simulated by stacking one or more sheets of water-equivalent material with a defined thickness (e.g., 0.25 in., 0.5 in., 1.0 in) above a dosimetric probe up to the simulated depth. The prescribed treatment dose of radiation may be applied to this set-up and the effective dose at the simulated target isocenter measured for quality assurance, before the patient is exposed to the radiological dose.

In one embodiment of a calibration device, the calibration device comprises 2.9-3.3% Glass Micro Bubbles (w/w), 54-67% Araldite (w/w), 20-33% Jeffamine (w/w), 3-5% $CaCO_1$ (w/w), 1-3% MgO (w/w), 8-12% Polyethylene (w/w), and 0-1% Pigment (w/w). In one embodiment, the calibration device comprises about 60-80% of the combination of Araldite and Jeffamine. The Araldite to Jeffamine ratio may be 10 to 4, 12.5 to 10 or 1 to 1. Thus within these ranges the Araldite and Jeffamine comprise the majority of the calibration device. The Jeffamine may have a molecular weight of about 440. The calibration device may further include about 3% calcium (provided as calcium carbonate) and about 2% magnesium (provided as magnesium oxide). The calibration device is made by mixing the dry constituents together prior to formation of the epoxy as described above.

Functional methods or operational sequences as described herein may be representative of exemplary embodiments, environments, and methodologies for performing novel aspects of the disclosure. While, for purposes of simplicity of explanation, the methodologies included herein may be in the form of a functional explanations, methods, or operational sequence, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events. Moreover, not all acts illustrated in as methodology may be required for as novel implementation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural or compositional elements with insubstantial differences from the literal languages of the claims.

I claim:

1. A composition for use in radiology comprising: 2.9-3.3% Glass Micro Bubbles (w/w), 60-90% of an epoxy, acrylic or polyurethane (w/w), 3-5% $CaCO_3$ (w/w), 1-3% MgO (w/w), and 8-12% Polyethylene (w/w):
    wherein the elemental composition comprises of 64-67% carbon (w/w), 18-21% oxygen (w/w), 7-10% hydrogen (w/w), 1-3.5% nitrogen (w/w), 0.5-3% calcium (w/w), 0.5-2.5% magnesium (w/w) and silicon, chlorine, boron, aluminum, sodium and sulfur at concentrations of less than 2% (w/w).

2. The composition of claim 1, each of the chlorine, boron, aluminum, sodium and sulfur are present at a concentration of less than 1% (w/w).

3. The composition of claim 1, further comprising a pigment at a concentration of 0-1.5% (w/w).

4. The composition of claim 3, wherein the pigment is selected from $Na_6Al_6Si_6O_{24}S_4$ or $Si_4O_{10}(OH)_2Mg_3$—$Co_3Ca$—Al.

5. The composition of claim 1, wherein the composition has a physical density of 1.03+/−0.03 g/cc.

6. The composition of claim 1, wherein the composition is a water phantom.

7. A method of calibrating a radiographic device, the method comprising:
    providing a phantom comprising the composition of claim 1;
    measuring an attenuation of radiation through the phantom; and
    calculating a correction factor for the radiographic device from the measured attenuation.

8. A composition for use in radiology comprising 3.09% (w/w) glass microbubbles, 57.88% (w/w) Araldite, 23.15% (w/w) Jeffamine, 3.89% (w/w) Calcium Carbonate ($CaCO_3$); 1.80% (w/w) Magnesium Oxide (MgO), 9.98% (w/w) Polyethylene (PE)(($C_2H_4$)$NH_2$), 0.2% (w/w) $Na_6Al_6Si_6O_{24}S_4$ or $Si_4O_{10}(OH)_2Mg_3$—$Co_3Ca$—Al with an elemental composition of 65.81% carbon (w/w), 19.36% oxygen (w/w), 8.14% hydrogen (w/w), 2.21% nitrogen (w/w), 1.78% calcium (w/w), 1.14% silicon (w/w), and 1.11% magnesium (w/w).

9. A method calibrating a radiographic device, the method comprising:
    providing a phantom comprising the composition of claim 8;
    measuring an attenuation of radiation through the phantom; and
    calculating a correction factor for the radiographic device from the measured attenuation.

10. The composition of claim 1, wherein the epoxy, acrylic or polyurethane is an epoxy resin system comprising an epoxy resin comprising Araldite and a hardener comprising Jeffamine, wherein the composition comprises 54-67% Araldite (w/w) and 20-33% Jeffamine (w/w).

11. The composition of claim 8, wherein the composition is a water phantom.

12. A composition for use in radiology comprising: 2.9-3.3% Glass Micro Bubbles (w/w), 60-90% of an epoxy, acrylic or polyurethane (w/w), 3-5% $CaCO_3$ (w/w), 1-3% MgO (w/w), 8-12% Polyethylene (w/w) and a pigment at a concentration of 0-1.5% (w/w), wherein the pigment is selected from $Na_6Al_6Si_6O_{24}S_4$ or $Si_4O_{10}(OH)_2Mg_3$—$Co_3Ca$—Al.

13. The composition of claim 12, wherein the elemental composition comprises of 64-67% carbon (w/w), 18-21% oxygen (w/w), 7-10% hydrogen (w/w), 1-3.5% nitrogen (w/w), 0.5-3% calcium (w/w), 0.5-2.5% magnesium (w/w).

14. The composition of claim 13, wherein the elemental composition further comprises at least one of silicon, chlorine, boron, aluminum, sodium and sulfur.

15. The composition of claim 14, wherein the silicon is at a concentration of 0.1-2.5% (w/w), and each of the chlorine, boron, aluminum, sodium and sulfur are present at a concentration of less than 1% (w/w).

16. The composition of claim 14, wherein the composition comprises silicon, chlorine, boron, aluminum, sodium and sulfur at concentrations of less than 2% (w/w).

17. The composition of claim 12, further comprising a pigment at a concentration of 0-1.5% (w/w).

18. The composition of claim 12, wherein the composition has a physical density of 1.03+/−0.03 g/cc.

19. The composition of claim 12, wherein the composition is a water phantom.

20. The composition of claim 12, wherein the epoxy, acrylic or polyurethane is an epoxy resin system comprising an epoxy resin comprising Araldite and a hardener comprising Jeffamine, wherein the composition comprises 54-67% Araldite (w/w) and 20-33% Jeffamine (w/w).

\* \* \* \* \*